US012533156B2

(12) United States Patent
Kitaoka et al.

(10) Patent No.: US 12,533,156 B2
(45) Date of Patent: Jan. 27, 2026

(54) MEDICAL DEVICE

(71) Applicant: TERUMO KABUSHIKI KAISHA, Tokyo (JP)

(72) Inventors: Takashi Kitaoka, San Jose, CA (US); Yuki Masubuchi, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 181 days.

(21) Appl. No.: 18/469,751

(22) Filed: Sep. 19, 2023

(65) Prior Publication Data

US 2024/0000479 A1 Jan. 4, 2024

Related U.S. Application Data

(63) Continuation of application No. PCT/JP2021/011491, filed on Mar. 19, 2021.

(51) Int. Cl.
*A61B 17/3207* (2006.01)

(52) U.S. Cl.
CPC ................. *A61B 17/320725* (2013.01); *A61B 2017/320741* (2013.01)

(58) Field of Classification Search
CPC .......... A61B 17/320725; A61B 17/221; A61B 2017/2212; A61B 2017/2215;
(Continued)

(56) References Cited

U.S. PATENT DOCUMENTS

| | | | |
|---|---|---|---|
| 10,779,852 | B2 | 9/2020 | Bruzzi et al. |
| 2016/0143652 | A1 | 5/2016 | Imai et al. |

(Continued)

FOREIGN PATENT DOCUMENTS

| | | | |
|---|---|---|---|
| JP | 2016097050 | A | 5/2016 |
| JP | 2016101315 | A | 6/2016 |

(Continued)

OTHER PUBLICATIONS

English Translations of the International Search Report (Form PCT/ISA/210) and the Written Opinion of the International Searching Authority (Form PCT/ISA/237) issued May 11, 2021, by the Japan Patent Office in corresponding International Application No. PCT/JP2021/011491. (5 pages).

(Continued)

*Primary Examiner* — Kathleen S Holwerda
(74) *Attorney, Agent, or Firm* — BUCHANAN INGERSOLL & ROONEY PC

(57) ABSTRACT

A medical device includes an expansion portion that rotates to break-up an object and that is prevented from receiving excessive force. The expansion portion is at a distal part of a shaft portion, a connection portion is fixed to a proximal part of the expansion portion, and an outer tube accommodates the shaft portion. The outer tube includes distal and proximal contact portions. The connection portion includes a first restricting portion distal to the distal contact portion and a second restricting portion proximal to the distal contact portion. An operation unit of the medical device includes a housing, a lever member fixed to the outer tube, and an elastic member that applies a force moving the outer tube in a distal direction to the outer tube. When the elastic member pushes the proximal contact portion in the distal direction, the distal contact portion is proximal to the first restricting portion.

20 Claims, 6 Drawing Sheets

(58) Field of Classification Search
CPC .... A61B 17/3207; A61F 2/0108; A61F 2/011; A61F 2/013
See application file for complete search history.

(56) References Cited

U.S. PATENT DOCUMENTS

| | | | | |
|---|---|---|---|---|
| 2016/0206344 | A1* | 7/2016 | Bruzzi | A61B 17/320758 |
| 2018/0296234 | A1 | 10/2018 | Eads et al. | |

FOREIGN PATENT DOCUMENTS

| | | | | | |
|---|---|---|---|---|---|
| JP | 2020516366 | A | | 6/2020 | |
| WO | WO-2019188655 | A1 | * | 10/2019 | A61B 17/221 |

OTHER PUBLICATIONS

International Search Report (PCT/ISA/210) with translation and Written Opinion (PCT/ISA/237) mailed on May 11, 2021, by the Japan Patent Office as the International Searching Authority for International Application No. PCT/JP2021/011491. (8 pages).

* cited by examiner

MEDICAL DEVICE

CROSS-REFERENCES TO RELATED APPLICATIONS

This application is a continuation of International Patent Application No. PCT/JP2021/011491 filed on Mar. 19, 2021, the entire content of which is incorporated herein by reference.

TECHNOLOGICAL FIELD

The present invention generally relates to a medical device used for removing an object in a living body lumen.

BACKGROUND DISCUSSION

When a thrombus is formed in the living body lumen, the formed thrombus needs to be quickly removed. Methods for treating a thrombosis include a method for breaking up and removing a thrombus by an expansion portion provided on a distal side of a long shaft portion. The expansion portion changes in the expanded diameter due to a change in length in the axial direction.

For example, U.S. Pat. No. 10,779,852 describes a device for removing thrombus. The device allows an expansion portion that can be expanded in the radial direction to be expandable in the radial direction by relatively moving, in the axial direction, a distal arm connected to the distal part of the expansion portion and a proximal arm connected to the proximal part of the expansion portion. Further, the proximal end of the distal arm and the proximal end of the proximal arm are directly connected by a spring to apply resistance to relative movement of the distal arm and the proximal arm.

SUMMARY

When the proximal end of the distal arm and the proximal end of the proximal arm are directly connected to each other with a spring, the spring constantly presses against the expansion portion due to a repulsive force constantly exerted by the spring, and thus, an excessive expansive force may occur. When the excessive expansive force is applied on the expansion portion, a body tissue such as a blood vessel wall may be damaged or the expansion portion may be deformed according to circumstances.

The medical device disclosed here is a highly safe medical device in which an expansion portion that rotates to break up an object is prevented from receiving excessive force.

A medical device according to the present invention for achieving the above object is a medical device for breaking up an object in a living body lumen, the medical device including: a long shaft portion to be rotationally driven; an expansion portion provided at a distal part of the shaft portion; a fixing portion to which a distal end of the expansion portion and the shaft portion are fixed; a connection portion fixed to a proximal end of the expansion portion and movable in an axial direction with respect to the shaft portion; an outer tube that accommodates the shaft portion and is movable in the axial direction along the shaft portion; and an operation unit to which a proximal part of the shaft portion is rotatably connected, wherein the outer tube includes a distal contact portion disposed at a distal part and protruding radially outward, and a proximal contact portion disposed at a proximal part, the connection portion includes a first restricting portion that is disposed distal to the distal contact portion and fixes the slide portion, and a second restricting portion that is disposed proximal to the distal contact portion and through which the distal contact portion is unable to pass, the operation unit includes a housing including an accommodating portion in which the proximal part of the shaft portion is disposed in a rotatable manner, a lever member that is fixed to the outer tube, is movable in the axial direction with respect to the housing, and is partially accommodated in the accommodating portion, and an acting member capable of applying a force that moves the outer tube in a distal direction to the outer tube by movement of the outer tube in a proximal direction, and when the acting member pushes the proximal contact portion or the lever member in the distal direction, the distal contact portion is located proximal to the first restricting portion.

In the medical device configured as described above, the distal contact portion is located proximal to the first restricting portion, so that the distal contact portion cannot press the first restricting portion in the distal direction. Therefore, a force for expanding the expansion portion does not act on the expansion portion from the acting member. Accordingly, application of excessive force on the expansion portion can be suppressed, whereby a body tissue and the expansion portion can be prevented from being damaged.

According to another aspect, a medical device positionable in a living body lumen to break-up an object in the living body lumen comprises a rotatable elongated shaft connectable to a motor so that operation of the motor results in rotation of the shaft, a plurality of circumferentially spaced apart wires each possessing a proximal end and a distal end, and a connector axially movable along the elongated shaft and having a distal portion connected to the proximal ends of the wires so that axial movement of the connector results in axial movement of the proximal ends of the wires relative to the distal ends of the wires to radially expand the wires as the proximal ends of the wires move toward the distal ends of the wires and radially contract the wires as the proximal ends of the wires move away from the distal ends of the wires. The distal end of each of the plurality of wires is fixed relative to the distal end of the elongated shaft so that rotation of the elongated shaft results in rotation of the plurality of wires, and the plurality of wires are movable into contact with the object in the living body lumen to break-up the object during rotation of the elongated shaft. A tube is axially movable relative to the elongated shaft and includes a projecting contact portion that is fixed relative to the tube so that axial movement of the tube results in axial movement of the projecting contact portion. The tube is axially movable relative to the connector in a proximal direction away from the wires until the projecting contact portion contacts a first part of the connector, and further axial movement of the tube relative to the connector in the proximal direction after the projecting contact portion contacts the first part of the connector results in axial movement of the connector in the proximal direction and radial contraction of the wires. The tube is axially movable relative to the connector in a distal direction toward the wires until the projecting contact portion contacts a second part of the connector located distal of the first part of the connector, and further axial movement of the tube relative to the connector in the proximal direction after the projecting contact portion contacts the first part of the connector results in axial movement of the connector in the proximal direction and radial contraction of the wire. A compressible elastic member is positioned to apply an elastic force to the tube when an external force external to the elastic member is applied to the elastic member so that the elastic member is in a compressed state. The elastic member is changeable from the compressed state to a natural state in which the external force is not applied to the elastic member, and the tube is axially movable in the distal direction relative to the elongated shaft when the elastic member is in the natural state.

Another aspect of the disclosure involves a medical device positionable in a living body lumen to break-up an object in the living body lumen in combination with a tubular sheath. The medical device comprises a rotatable elongated shaft connectable to a motor so that operation of the motor results in rotation of the shaft, a plurality of circumferentially spaced apart wires, and a connector axially movable along the elongated shaft. Each of the wires possesses a proximal end and a distal end, with the distal end of each of the plurality of wires being fixed relative to the distal end of the elongated shaft so that rotation of the elongated shaft results in rotation of the plurality of wires, and wherein the plurality of wires are movable into contact with the object in the living body lumen to break-up the object during operation of the motor. The connector axially movable along the elongated shaft and has a distal portion connected to the proximal ends of the wires so that axial movement of the connector results in axial movement of the proximal ends of the wires relative to the distal ends of the wires to radially expand the wires as the proximal ends of the wires move toward the distal ends of the wires and radially contract the wires as the proximal ends of the wires move away from the distal ends of the wires. A tube is axially movable relative to the elongated shaft and includes a projecting contact portion that is fixed relative to the tube so that axial movement of the tube results in axial movement of the projecting contact portion. The tube is axially movable relative to the connector in a proximal direction away from the wires until the projecting contact portion contacts a first part of the connector, with further axial movement of the tube relative to the connector in the proximal direction after the projecting contact portion contacts the first part of the connector resulting in axial movement of the connector in the proximal direction and radial contraction of the wires. The tube being axially movable relative to the connector in a distal axial direction toward the wires until the projecting contact portion contacts a second part of the connector located distal of the first part of the connector, with further axial movement of the tube relative to the connector in the proximal direction after the projecting contact portion contacts the first part of the connector resulting in axial movement of the connector in the proximal direction and radial contraction of the wire. The medical device also includes a compressible elastic member that is in a natural state when no external force external to the elastic member is applied to the elastic member. The elastic member is changeable from the natural state to a compressed state when the external force external to the elastic member is applied to the elastic member to compress the elastic member, and the elastic member is positioned to apply an elastic force to the tube when the elastic member is in the compressed state. The plurality of wires: i) are positionable inside the tubular sheath while the wires are radially contracted as a result of the axial movement of the tube relative to the connector in the proximal direction after the projecting contact portion contacts the first part of the connector so that the wires contact an inner periphery of the tubular sheath; and ii) when positioned inside the tubular sheath are releasable from the tubular sheath so that the wires expand by their own elastic force and return to a natural state allowing the wires to be brought into contact with the object in the living body lumen. When the wires are positioned in the tubular sheath, a force in the distal axial direction from the elastic member does not act on the tube.

BRIEF DESCRIPTION OF THE DRAWINGS

FIGS. 2A and 2B are cross-sectional views illustrating the medical device in a first state in which an expansion portion is expanded, in which FIG. 2A illustrates a distal part of the medical device, and FIG. 2B illustrates a proximal part of the medical device.

FIGS. 3A and 3B are cross-sectional views illustrating the medical device in a second state in which the expansion portion is contracted, in which FIG. 3A illustrates the distal part of the medical device, and FIG. 3B illustrates the proximal part of the medical device.

FIGS. 4A and 4B are cross-sectional views illustrating the medical device in a fourth state in which the contracted expansion portion is expanded within a sheath, in which FIG. 4A illustrates the distal part of the medical device, and FIG. 4B illustrates the proximal part of the medical device.

FIGS. 5A and 5B are cross-sectional views illustrating the medical device in the fourth state in which an outer tube and a lever member move away from an elastic member, in which FIG. 5A illustrates the distal part of the medical device, and FIG. 5B illustrates the proximal part of the medical device.

FIGS. 6A and 6B are cross-sectional views illustrating the medical device in a fifth state in which the expansion portion is contracted in a blood vessel, in which FIG. 6A illustrates the distal part of the medical device, and FIG. 6B illustrates the proximal part of the medical device.

DETAILED DESCRIPTION

Figure 1:
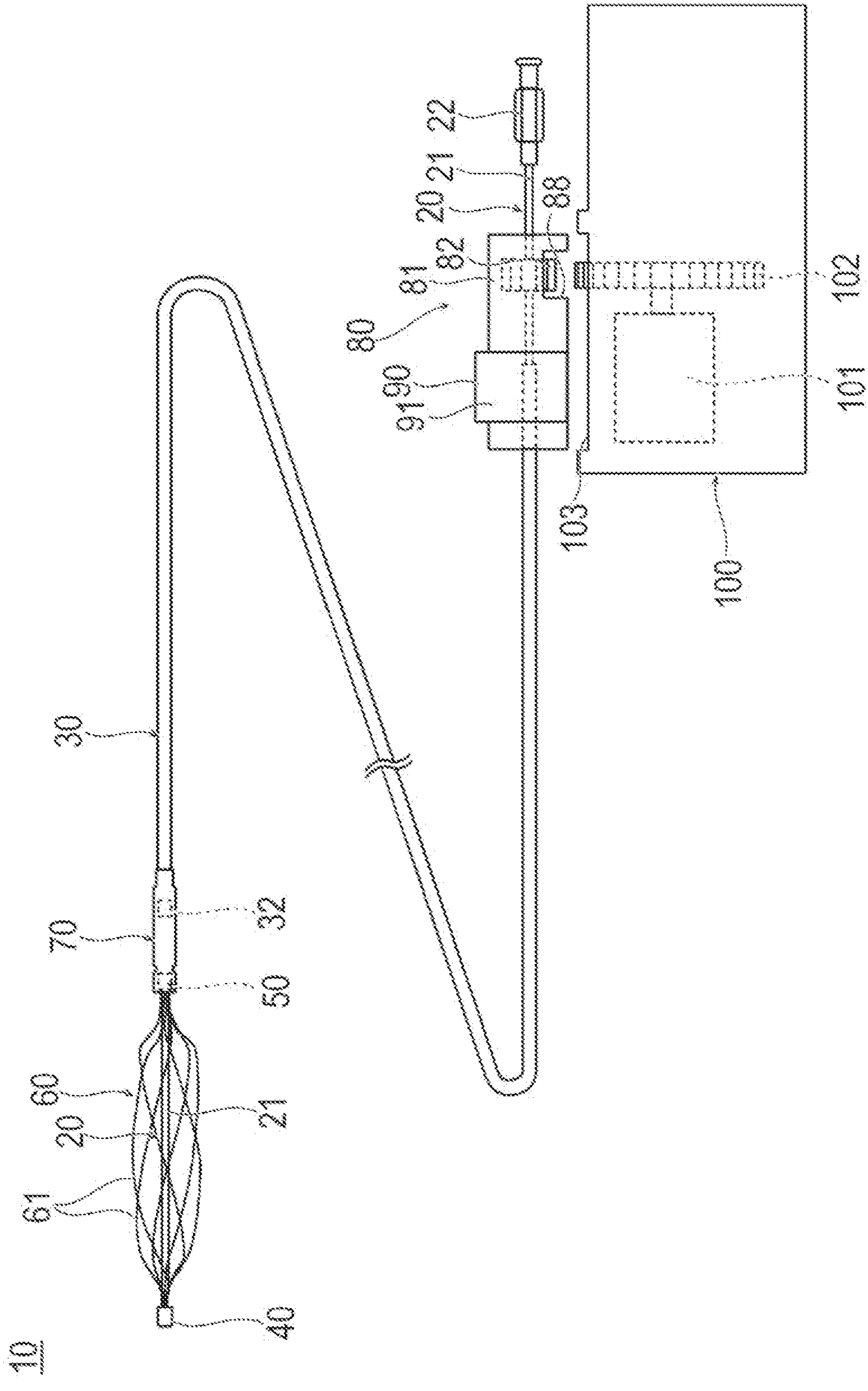
FIG. 1 is a plan view illustrating a medical device according to an embodiment.

An embodiment of the medical device disclosed here, representing an example of the new medical device, will be described below with reference to the drawings. Dimensional ratios in the drawings may be exaggerated and different from actual ratios for convenience of description.

A medical device 10 according to the present embodiment is inserted into a blood vessel and used for a treatment involving breaking up a thrombus in deep venous thrombosis treatment. Herein, a side of the device to be inserted into a blood vessel is referred to as "distal side" and a side to be operated is referred to as "proximal side." The object to be broken up is not necessarily limited to the thrombus, and may be any object that can be present in the living body lumen. Breaking up means breaking an object by a structure, and a shape of the structure, a breaking method, a degree of breaking, a range of breaking, a shape of the broken object, and the like are not limited.

As illustrated in FIGS. 1 and 2, the medical device 10 includes a shaft portion 20, an outer tube 30, an expansion portion 60, a fixing portion 40, a slide portion 50, a connection portion 70, an operation unit 80, and a drive unit 100.

The shaft portion 20 is a section that transmits a rotational force to the expansion portion 60. The shaft portion 20 includes a shaft body 21 and a hub 22.

The shaft body 21 is a long tubular body (elongated tubular member) that transmits rotational force from the proximal part to the distal part. The proximal part of the shaft body 21 penetrates the operation unit 80. The proximal part of the shaft body 21 is disposed in the operation unit 80 so as to be rotatable. The shaft body 21 has flexibility so as to be movable in a blood vessel. Further, the shaft body 21 preferably has high torsional rigidity so that rotational forces can be transmitted from the proximal part to the distal part. The shaft body 21 is, for example, a metal tubular body having a helical slit formed therein. A material from which the shaft body 21 may be fabricated is preferably, for example, stainless steel or the like.

The hub 22 is fixed to the proximal end of the shaft body 21. A guide wire 120 can be inserted into or positioned in the hub 22.

The fixing portion 40 is a ring-shaped member that fixes the expansion portion 60 to the shaft portion 20. The fixing portion 40 is fixed to the outer peripheral surface of the shaft body 21 at the distal end of the shaft body 21. The fixing portion 40 is also fixed to the distal end of the expansion portion 60.

The slide portion 50 is a ring-shaped member provided proximal to the fixing portion 40 on the outer peripheral surface of the shaft body 21 so as to be slidable in the axial direction. The slide portion 50 is fixed to the proximal end of the expansion portion 60.

The expansion portion 60 is a section that expands in the living body lumen and rotates to break up an object such as a thrombus. The expansion portion 60 is provided at a distal part of the shaft portion 20. The expansion portion 60 includes a plurality of (six in the present embodiment) wire rods 61. Each wire rod 61 is three-dimensionally curved. The number of the wire rods 61 is not particularly limited. The cross-sectional shape of the wire rod 61 is not particularly limited. Each of the wire rods 61 is twisted in the same circumferential direction along the axial direction of the shaft portion 20. The distal end of each wire rod 61 is fixed to the fixing portion 40. The proximal end of each wire rod 61 is fixed to the slide portion 50. The fixing positions where the wire rods 61 are fixed to the fixing portion 40 and the slide portion 50 are arranged in the circumferential direction. The substantially central portions, which are curved, of the respective wire rods 61 are arranged in the circumferential direction at positions distant from the shaft portion 20 in the radial direction. With this configuration, the expansion portion 60 uniformly expands in the circumferential direction as a whole. The expansion portion 60 expands in the radial direction in a natural state where no external force acts. When the shaft portion 20 rotates, the expansion portion 60 also rotates accordingly, and can break up a thrombus in the blood vessel or stir the thrombus that has been broken up. The expansion portion 60 is contracted in the radial direction by receiving a force for separating both ends in the axial direction. Alternatively, the expansion portion 60 is contracted in the radial direction by receiving a force from the outside to the inside in the radial direction.

Figure 3A:
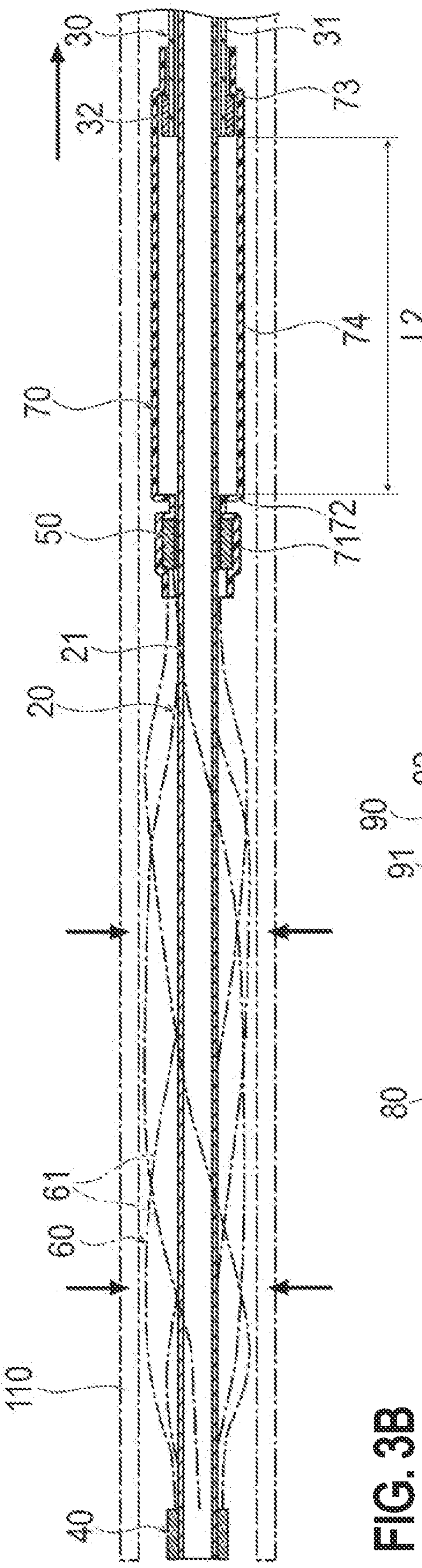

The wire rods 61 constituting the expansion portion 60 are formed of a thin metal wire having flexibility. As illustrated in FIGS. 3 to 5, the expansion portion 60 is accommodated inside a known sheath 110 until reaching a target site in the blood vessel. When the expansion portion 60 is inserted into the sheath 110, the slide portion 50 moves to the proximal side along the shaft portion 20 and away from the fixing portion 40. Thus, the wire rods 61 are reduced in diameter and accommodated in the sheath 110. After the shaft portion 20 is inserted and carried to the target site in the blood vessel, the sheath 110 is moved to the proximal side with respect to the shaft portion 20. As a result, the expansion portion 60 is exposed to the outside of the sheath 110 and expands by its own elastic force as illustrated in FIGS. 1 and 2. At this time, the slide portion 50 moves to the distal side along the shaft portion 20.

The wire rods 61 are desirably made of a material having a shape memory property so as to be elastically largely deformable. Preferable examples of the material of the wire rods 61 include a shape memory alloy to which a shape memory effect or superelasticity is imparted by heat treatment, and stainless steel. As the shape memory alloy, a Ni—Ti-based alloy, a Cu—Al—Ni-based alloy, a Cu—Zn—Al-based alloy, a combination thereof, or the like is suitable.

The outer tube 30 is a member that transmits a moving force in the axial direction on the proximal side to the distal side. The axial direction is a long (elongated) direction of the medical device 10, and is a direction in which the central axes of the outer tube 30 and the shaft body 21 extend. The outer tube 30 includes an outer tube body 31, a distal contact portion 32, and a proximal contact portion 33. The outer tube body 31 is a tubular body that accommodates the rotating shaft body 21 in a rotatable manner. The outer tube body 31 has flexibility so as to be movable in a blood vessel. The outer tube body 31 is movable in the axial direction along the shaft body 21. The proximal part of the outer tube body 31 is located inside the operation unit 80. The distal contact portion 32 is a ring-shaped member fixed to the outer peripheral surface of the outer tube body 31 at the distal part. The distal contact portion 32 protrudes radially outward from the outer peripheral surface of the outer tube body 31. The proximal contact portion 33 is a ring-shaped member fixed to the outer peripheral surface of the outer tube body 31 at the proximal part. The proximal contact portion 33 protrudes radially outward from the outer peripheral surface of the outer tube body 31. The proximal contact portion 33 may be a proximal end face of the outer tube body 31. That is, the proximal contact portion 33 may not protrude radially outward from the outer peripheral surface of the outer tube body 31.

The connection portion 70 is a tubular body that transmits a moving force in the axial direction of the outer tube 30 to the slide portion 50. The connection portion 70 includes a distal-side fixing portion 71, a first restricting portion 72, a second restricting portion 73, and a cylindrical portion 74.

The distal-side fixing portion 71 covers the slide portion 50 fixed to the proximal end of the expansion portion 60 and is fixed to the slide portion 50.

The first restricting portion 72 is located proximal to the distal-side fixing portion 71 and distal to the cylindrical portion 74. The inner peripheral surface of the first restricting portion 72 is close to the outer peripheral surface of the shaft body 21 with a predetermined clearance. The inner peripheral surface of the first restricting portion 72 can smoothly slide on the outer peripheral surface of the shaft body 21.

The second restricting portion 73 is located proximal to the cylindrical portion 74. The inner peripheral surface of the second restricting portion 73 is close to the outer peripheral surface of the outer tube body 31 with a predetermined clearance. The inner peripheral surface of the second restricting portion 73 can smoothly slide on the outer peripheral surface of the outer tube body 31.

The cylindrical portion 74 is a cylindrical section located between the first restricting portion 72 and the second restricting portion 73. The inner diameter of the cylindrical portion 74 is larger than the outer diameter of the distal contact portion 32. Accordingly, the cylindrical portion 74 provides an internal space in which the distal contact portion 32 is movable in the axial direction. The first restricting portion 72 disposed distal to the internal space restricts the movement of the distal contact portion 32 to the distal side in the cylindrical portion 74. The first restricting portion 72 may not have a function of restricting the movement of the distal contact portion 32 to the distal side, and is only required to have a function of fixing the slide portion 50 and the distal-side fixing portion 71. Fixing the slide portion 50 and the distal-side fixing portion 71 includes not only fixing them such that they are connected to each other by adhesion, fusion, fitting, or the like, but also bringing them in contact with each other so as to be integrally movable in the axial direction without connection. The second restricting portion 73 disposed proximal to the internal space restricts the movement of the distal contact portion 32 to the proximal side in the cylindrical portion 74. The first restricting portion 72 and the second restricting portion 73 are heated in a state of being covered with a heat shrinkable tube, and is reduced in inner and outer diameters by the heat shrinkable tube that is reduced in diameter. Alternatively, the first restricting portion 72 and the second restricting portion 73 may be formed of a heat shrinkable tube, and may be reduced in inner and outer diameters by being heated. As illustrated in FIG. 3, the cylindrical portion 74 has, as a distal-side displaceable length L2, a length over which the distal contact portion 32 can move in the axial direction in the cylindrical portion 74. The distal-side displaceable length L2 is a length obtained by subtracting the length of the distal contact portion 32 in the axial direction from the distance between the first restricting portion 72 and the second restricting portion 73 in the axial direction.

The connection portion 70 is preferably more flexible than the shaft portion 20 and has lower flexural rigidity so as not to hinder the movement of the shaft portion 20. The material of which the connection portion 70 may be fabricated is not particularly limited, and examples of the material that can be preferably used include thermoplastic polyester elastomer, polyolefin such as polyethylene and polypropylene, polyamide, polyester such as polyethylene terephthalate, fluorine-based polymer such as polytetrafluoroethylene (PTFE) and tetrafluoroethylene-ethylene copolymer (ETFE), polyetheretherketone (PEEK), and polyimide.

The operation unit 80 is a section gripped and operated by an operator. The operation unit 80 includes a housing 81, a first gear 82 fixed to the shaft body 21, a bearing 83 that rotatably supports the shaft body 21, an elastic member 84 (acting member) that applies a force to the outer tube 30, and a lever member 90 for operating the outer tube 30 as illustrated in FIGS. 1 and 2.

The housing 81 is penetrated by the shaft portion 20 and accommodates the proximal end of the outer tube 30 therein. The housing 81 includes an accommodating portion 85 that accommodates the lever member 90 and the elastic member 84 so as to be movable in the axial direction, and a gear accommodating portion 86 that accommodates the first gear 82 so as to be rotatable. A support surface 87 that supports the proximal end of the elastic member 84 is formed at the proximal part of the accommodating portion 85. The support surface 87 can support the proximal end of the elastic member 84 and can move away from the elastic member 84.

The lever member 90 includes a lever operation portion 91 which is located outside the housing 81 and operated by the operator, and an inner sliding portion 92 which enters (extends into) the accommodating portion 85 from the lever operation portion 91. The lever member 90 is movable in the axial direction with respect to the housing 81. The inner sliding portion 92 includes an outer tube fixing portion 93 through which the outer tube 30 penetrates and is fixed, and an accommodation hole 94 disposed proximal to the outer tube fixing portion 93 and having an inner diameter larger than that of the outer tube fixing portion 93. Fixing the lever member 90 and the outer tube 30 includes not only fixing them such that they are connected to each other by adhesion, fusion, fitting, or the like, but also bringing them in contact with each other so as to be integrally movable in the axial direction without connection. The proximal contact portion 33 of the outer tube 30 and a part of the distal side of the elastic member 84 can be located inside the accommodation hole 94. An inner diameter of the outer tube fixing portion 93 is smaller than an outer diameter of the proximal contact portion 33. Therefore, the proximal contact portion 33 disposed inside the accommodation hole 94 can contact the proximal surface of the outer tube fixing portion 93 and cannot pass through the outer tube fixing portion 93 to the distal side. The outer tube fixing portion 93 may be a part of the lever member 90.

The elastic member 84 is a member that is accommodated in the accommodating portion 85 and presses the proximal contact portion 33 of the outer tube 30 to the distal side. The elastic member 84 is, for example, a coil spring, and is wound around the shaft body 21 penetrating the accommodating portion 85. The proximal end of the elastic member 84 can come into contact with the support surface 87 of the accommodating portion 85 and can move away from the support surface 87. The distal end of the elastic member 84 can come into contact with the proximal end face of the proximal contact portion 33 of the outer tube 30 and can move away from the proximal contact portion 33.

The first gear 82 is partially disposed in the gear accommodating portion 86 of the housing 81 and is partially exposed to the outside from an opening 88 of the housing 81.

The bearing 83 is disposed on both the distal side and the proximal side with respect to the first gear 82 and supports the shaft portion 20 in a rotatable manner with respect to the housing 81.

The drive unit 100 is a section that rotationally drives the shaft portion 20. The drive unit 100 includes a drive source 101 such as a motor, a second gear 102 rotated by the drive source 101, and a connector 103 connected to the operation unit 80. When the connector 103 is connected to the operation unit 80, the second gear 102 meshes with the first gear 82. Thus, the shaft portion 20 can be rotated by rotating the drive source 101. The drive source 101 can reciprocate in the rotation direction. The drive source 101 is not limited to reciprocating, and may rotate in one direction.

Next, the operation of the medical device 10 according to the embodiment will be described, taking a case of breaking up a thrombus B (see FIG. 6) in the blood vessel as an example.

First, as illustrated in FIG. 2, the medical device 10 in which the expansion portion 60 expands in a natural state is prepared. This state of the medical device 10 is defined as a first state. In the first state, the elastic member 84 in the accommodating portion 85 extends in a natural state.

Figure 3B:
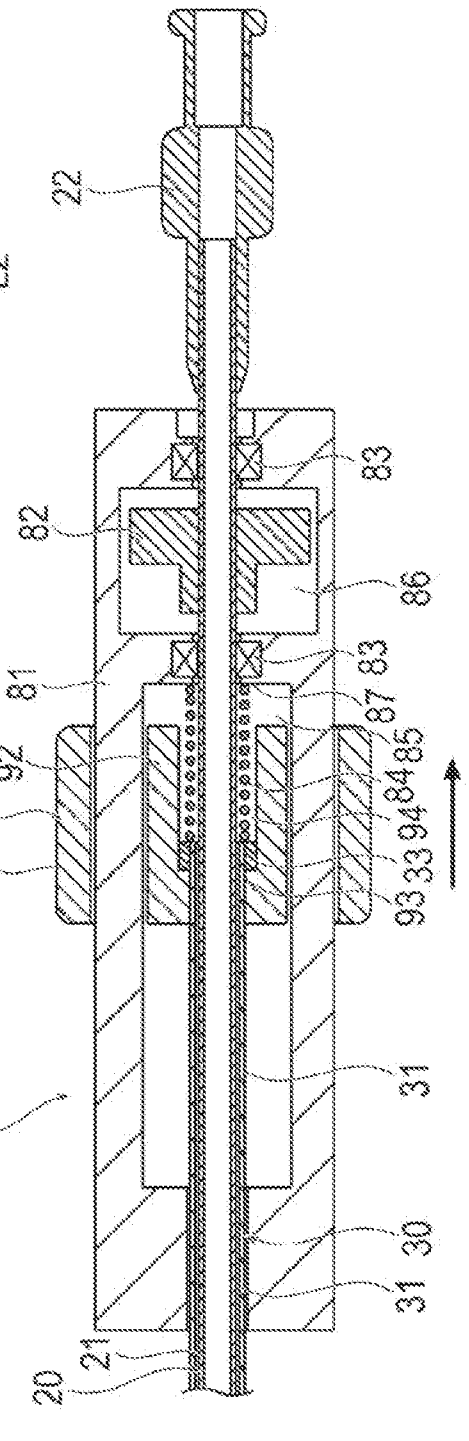
Figure 4A:
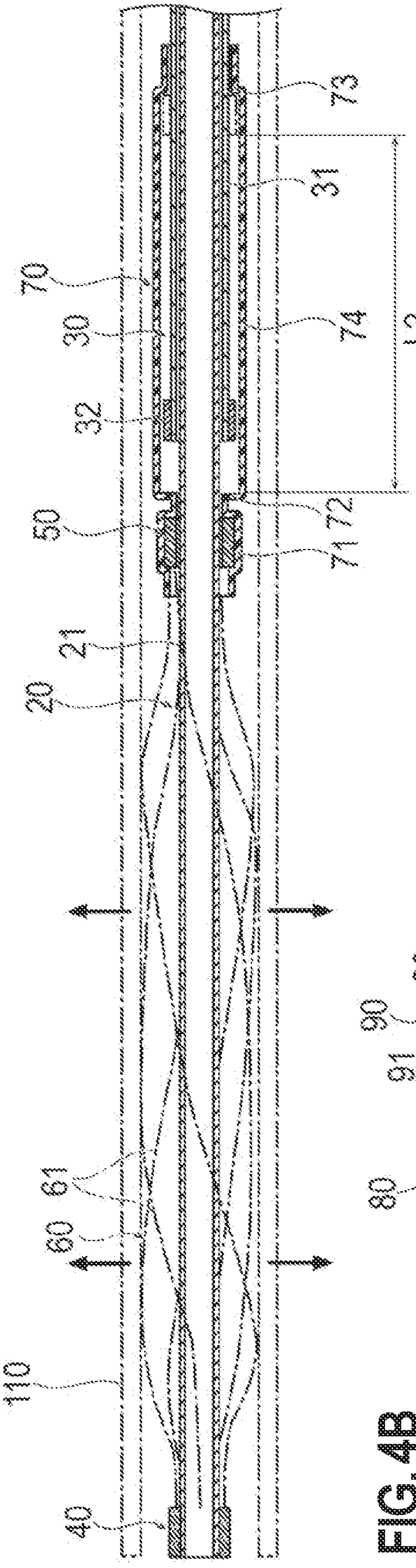

Next, as illustrated in FIG. 3(B), the operator moves the lever member 90 of the operation unit 80 to the proximal side with respect to the housing 81. As a result, the proximal contact portion 33 of the outer tube 30 moves to the proximal side together with the lever member 90. The proximal contact portion 33 or the lever member 90 comes into contact with the elastic member 84 disposed on the proximal side and moves the elastic member 84 to the proximal side in the axial direction while contracting the elastic member 84. Therefore, the operator can move the outer tube 30 to the proximal side by moving the lever member 90 to the proximal side against the repulsive force of the elastic member 84.

When the outer tube 30 moves to the proximal side, the distal contact portion 32 of the outer tube 30 moves inside the cylindrical portion 74, comes into contact with the second restricting portion 73, and pushes the second restricting portion 73 to the proximal side as illustrated in FIG. 3(A). Thus, the connection portion 70 moves to the proximal side with respect to the shaft body 21, and the slide portion 50 fixed to the distal-side fixing portion 71 of the connection portion 70 slides on the outer peripheral surface of the shaft body 21 to the proximal side. As a result, the slide portion 50 to which the proximal part of the expansion portion 60 is fixed moves to the proximal side and is away from the fixing portion 40 to which the distal part of the expansion portion 60 is fixed. Consequently, the expansion portion 60 is elastically deformed and contracted in the radial direction. This state of the medical device 10 is defined as a second state. In the second state, a part of the expansion portion 60 is contracted smaller than the inner diameter of the sheath 110. Note that another part of the expansion portion 60 is not contracted smaller than the inner diameter of the sheath 110. When the contracted expansion portion 60 is drawn into the sheath 110, a part of the expansion portion 60 larger than the inner diameter of the sheath 110 elastically contracts and is drawn into the sheath 110. A state of the medical device 10 in which the expansion portion 60 is inserted into the sheath 110 by the operator moving the lever member 90 of the operation unit 80 to the proximal side with respect to the housing 81 is defined as a third state. In the third state, the proximal contact portion 33 or the lever member 90 comes into contact with the elastic member 84 located on the proximal side, and presses the elastic member 84 to the proximal side, thereby contracting the elastic member 84 along the axial direction. In the second state before the expansion portion 60 is inserted into the sheath 110, a part of the expansion portion 60 is contracted smaller than the inner diameter of the sheath 110, and thus, the operator can easily insert the contracted expansion portion 60 into the sheath 110. Therefore, as compared with a case where the expansion portion 60 in the expanded state is forcibly inserted into the sheath 110, the application of excessive force on the expansion portion 60 can be suppressed, whereby the damage of the expansion portion 60 and the damage of the distal end of the sheath 110 can be prevented. The distal end of the sheath 110 which has a distal tip formed of a flexible material is likely to be damaged in the case where the expansion portion 60 in the expanded state is forcibly inserted into the sheath 110, but can be prevented from being damaged by reducing the force received from the expansion portion 60.

Figure 4B:
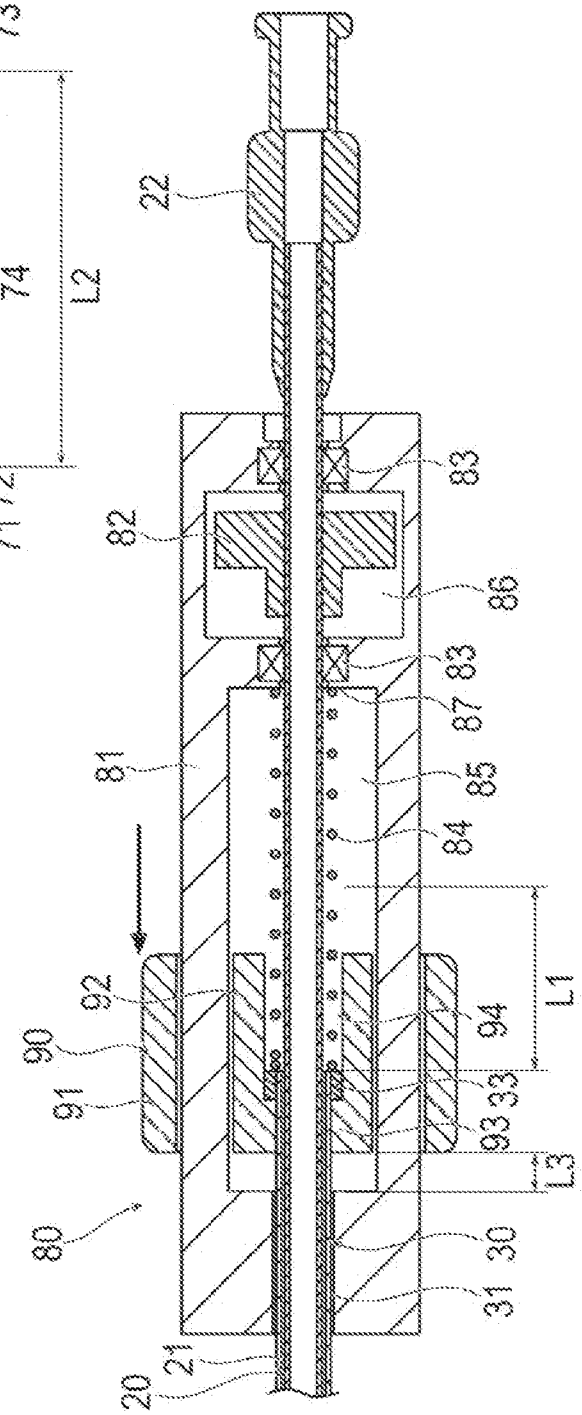
Figure 5A:
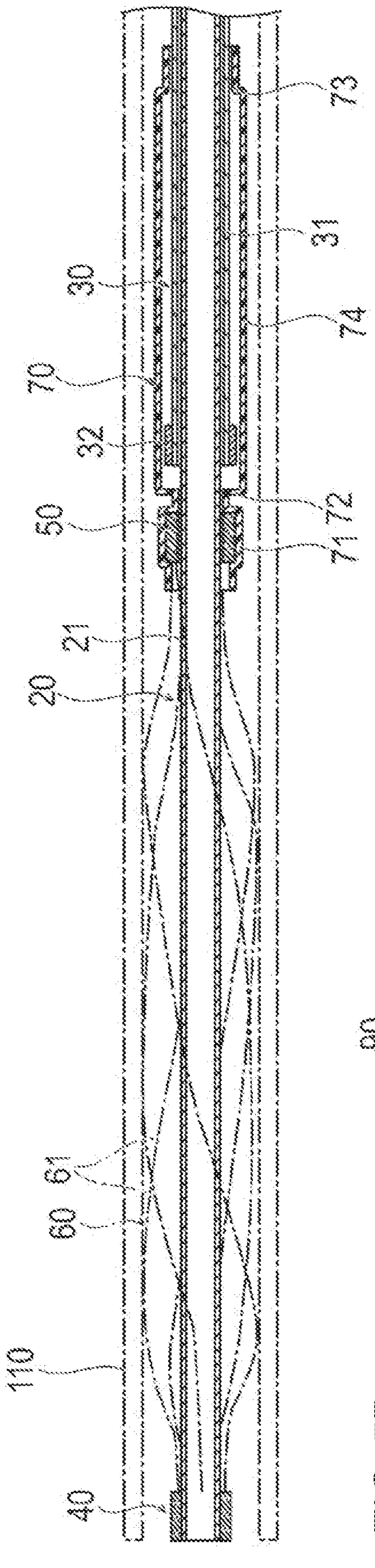
Figure 5B:
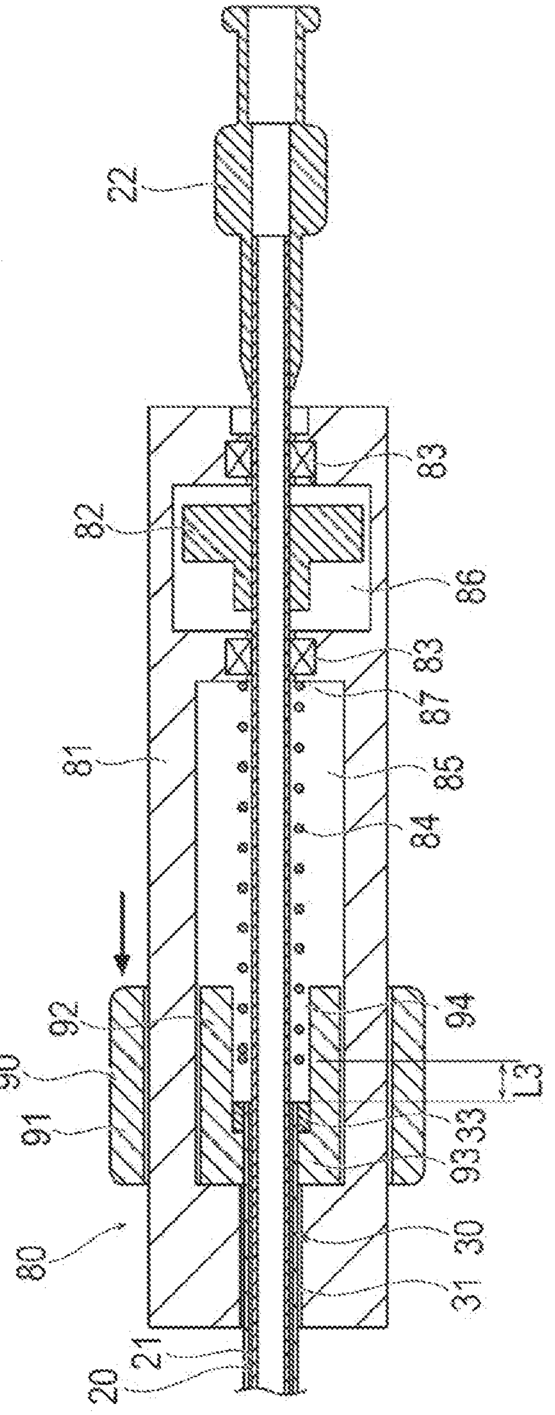

Next, when the operator releases the finger from the lever operation portion 91, the inner sliding portion 92 and the proximal contact portion 33 that have pressed the elastic member 84 to the proximal side in the accommodating portion 85 as illustrated in FIG. 3(B) are pushed and moved to the distal side by the elastic member 84 that is released from the restraint by the lever member 90 and extends as illustrated in FIG. 4(B). The elastic member 84 extends a force action length L1 from the state of being contracted in the axial direction illustrated in FIG. 3(B) to the natural state illustrated in FIG. 4(B) in which the external force does not act. The force action length L1 is a length of a region in which the elastic member 84 can apply a force to the outer tube 30 along the axial direction. The expansion portion 60 is disposed inside the sheath 110 as illustrated in FIG. 4(A), and thus, the expansion portion slightly expands in the radial direction so as to be held in contact with the inner peripheral surface of the sheath 110. This state of the medical device 10 is defined as a fourth state. As illustrated in FIGS. 4(B) and 5(B), the accommodating portion 85 has a movement allowable length L3 over which the inner sliding portion 92 and the proximal contact portion 33 can freely move in the axial direction without being pressed from the elastic member 84 when the elastic member 84 is in the natural state. Therefore, in the fourth state, no force in the axial direction acts on the outer tube 30 from the elastic member 84. In the fourth state, the inner sliding portion 92 and the proximal contact portion 33 inside the accommodating portion 85 may be moved inside the gear accommodating portion 86 to the innermost part on the distal side as illustrated in FIG. 5B without receiving a repulsive force from the elastic member 84.

In the fourth state, the force action length L1 is shorter than the distal-side displaceable length L2. Therefore, as illustrated in FIG. 4(A), the distal contact portion 32 of the outer tube 30 currently receiving a force from the elastic member 84 cannot reach the first restricting portion 72 of the connection portion 70. Thus, the elastic force of the elastic member 84 cannot act on the first restricting portion 72 via the outer tube 30, by which a force for expanding the expansion portion 60 accommodated in the sheath 110 does not act on the expansion portion 60 from the elastic member 84. Accordingly, application of excessive force on the expansion portion 60 within the sheath 110 can be suppressed, whereby damage of the expansion portion 60 and damage of the sheath 110 can be prevented.

Next, the operator inserts the guide wire 120 (see FIG. 6) into the shaft portion 20. Then, the operator brings the expansion portion 60 to the vicinity of the thrombus B along the guide wire 120. The operator then moves the sheath 110 to the proximal side relative to the medical device 10 to release the expansion portion 60 outside of the sheath 110. At this time, the expansion portion 60 receives no force from the elastic member 84, so that friction with the sheath 110 is small. Therefore, the expansion portion is easily released from the sheath 110. The operator may move the lever member 90 of the operation unit 80 to the proximal side with respect to the housing 81 before releasing the expansion portion 60 from the sheath 110, and temporarily bring the medical device 10 into the above-described third state (see FIGS. 3A and 3B). Thus, a part of the expansion portion 60 contracts smaller than the inner diameter of the sheath 110, and the expansion portion 60 is easily released from the sheath 110.

Figure 2A:
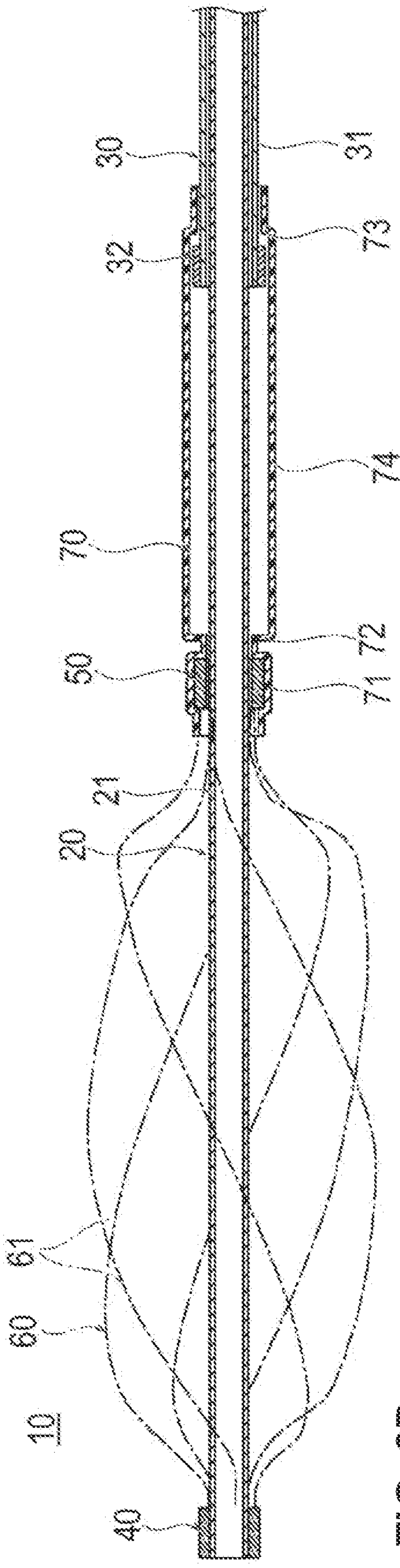
Figure 2B:
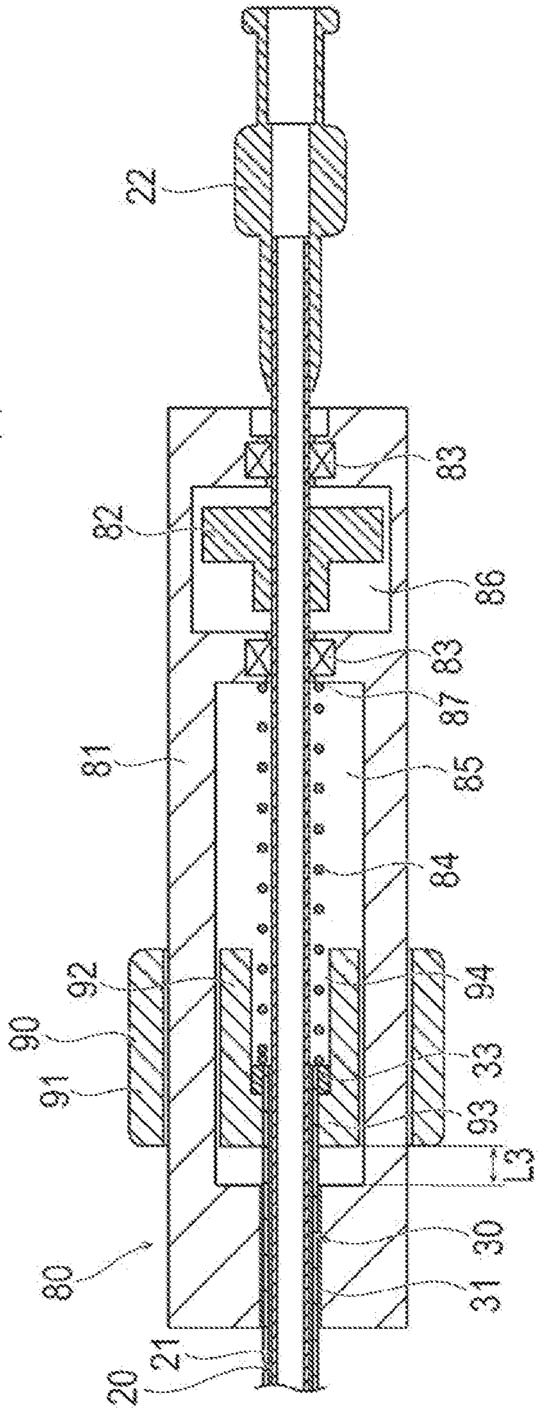

When the expansion portion 60 is released from the sheath 110, the medical device 10 is in the first state as illustrated in FIGS. 2A and 2B. At this time, the elastic force of the elastic member 84 does not act on the expansion portion 60, so that the length of the elastic member 84 does not change. When released from the sheath 110, the expansion portion 60 expands by its own elastic force and returns to a natural state as illustrated in FIG. 2(A). When the expansion portion 60 returns to its natural state, the connection portion 70 connected to the proximal part of the expansion portion 60 is pulled by the expansion portion 60 that contracts in the axial direction, thereby moving to the distal side along the shaft body 21. At this time, the outer tube 30 does not move with respect to the shaft body 21, or even if the outer tube 30 moves, it moves within a range of the movement allowable length L3 in which the outer tube 30 does not receive a repulsive force from the elastic member 84 as illustrated in FIG. 2(B). Therefore, the expansion portion 60 expands only by its own elastic force without receiving a force from the elastic member 84 as illustrated in FIGS. 2A and 2B, whereby the expansive force is not excessive, and the blood vessel can be prevented from being damaged. In addition, concentration of excessive stress on the expansion portion 60 can be suppressed, whereby damage of the expansion portion 60 and damage of the sheath 110 at the distal end can be prevented. In addition, since the distal contact portion 32 is separated from the first restricting portion 72 and is separated from the second restricting portion 73, the connection portion 70 can move within a certain range in the axial direction without receiving a force from the elastic member 84 via the outer tube 30. Therefore, the expansion portion 60 can be deformed slightly larger or slightly smaller from the expanded state without receiving a force from the elastic member 84.

Next, the drive unit 100 is connected to the operation unit 80 as illustrated in FIG. 1. Next, when the drive source 101 is operated, the shaft portion 20 rotates, and the expansion portion 60 fixed to the shaft portion 20 by the fixing portion 40 rotates. Then, when the expansion portion 60 is reciprocated in the axial direction in the blood vessel, the expansion portion 60 comes into contact with the thrombus B and breaks up the thrombus B. The expansion portion 60 is operated to alternate between rotating during which the expansion portion 60 rotates and not rotating during which the expansion portion 60 does not rotate (i.e., rotation of the expansion portion 60 is stopped) in a repeated manner. As a result, the expansion portion 60 repeats the operation of biting into the thrombus B when stopped and scraping the thrombus B by rotation.

Figure 6A:
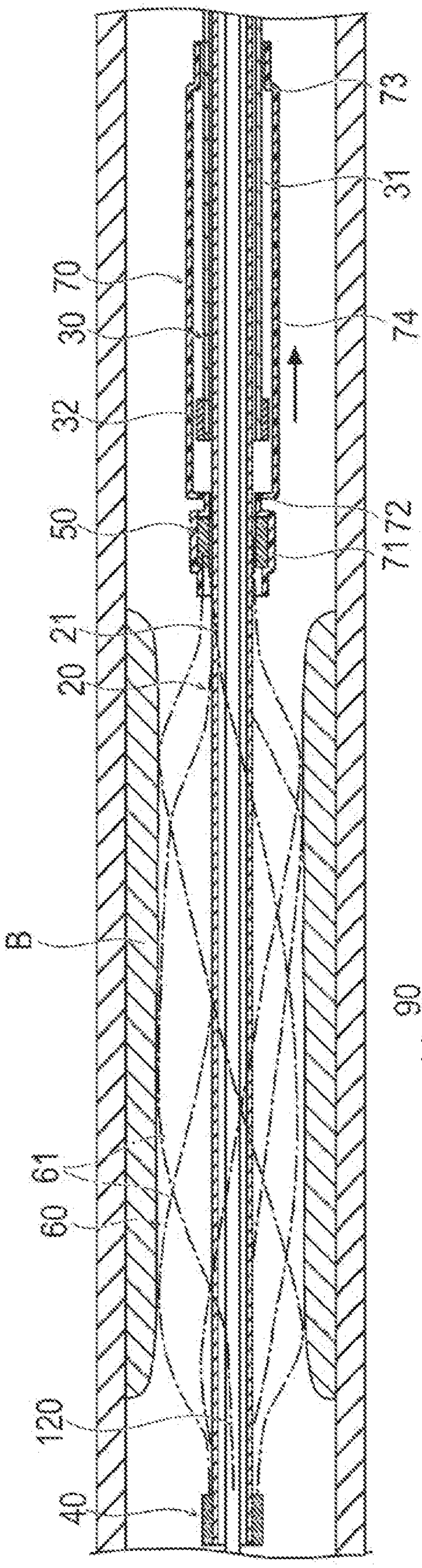
Figure 6B:
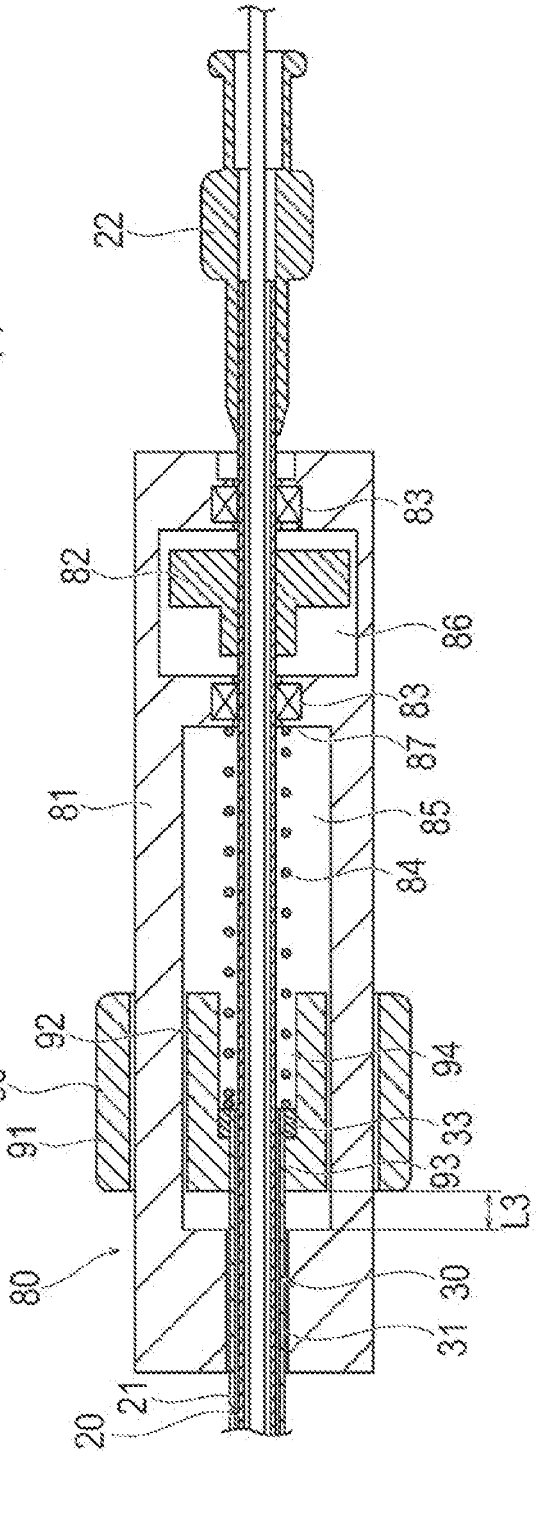

As illustrated in FIG. 6, when entering a narrow lesion having the thrombus B, the expansion portion 60 may be contracted in the radial direction by receiving a force from the outside in the radial direction. This state of the medical device 10 is defined as a fifth state. At this time, the connection portion 70 connected to the proximal part of the expansion portion 60 moves to the proximal side along the shaft body 21. The outer tube 30 does not move with respect to the shaft body 21, or even if the outer tube 30 moves, it moves within a range of the movement allowable length L3 in which the outer tube 30 does not receive a repulsive force from the elastic member 84 as illustrated in FIG. 6(B). Therefore, the expansion portion 60 expands only by its own elastic force without receiving a force from the elastic member 84, whereby the expansive force is not excessive, and the blood vessel can be prevented from being damaged. In addition, concentration of excessive stress on the expansion portion 60 can be suppressed, whereby the expansion portion 60 can be prevented from being damaged.

After breaking up the thrombus B by the expansion portion 60, the operator stops the drive source 101 to stop the rotation of the shaft portion 20. Then, the operator may place the expansion portion 60 in the sheath 110 in a manner similar to the manner of placing the expansion portion 60 in the sheath 110 prior to the procedure described with reference to FIGS. 3A and 3B. That is, the operator can accommodate the expansion portion 60 in the sheath 110 after moving the lever member 90 to the proximal side with respect to the housing 81 to radially contract the expansion portion 60. As a result, the medical device 10 enters the third state illustrated in FIGS. 3A and 3B after entering the second state described above. In the second state before the third state, a part of the expansion portion 60 is contracted smaller than the inner diameter of the sheath 110, and thus, the operator can easily accommodate the contracted expansion portion 60 into the sheath 110. Therefore, as compared with a case where the expansion portion 60 in the expanded state is forcibly accommodated into the sheath 110, the application of excessive force on the expansion portion 60 can be suppressed, whereby the damage of the expansion portion 60 and the damage of the sheath 110 at the distal end can be prevented. When the operator releases the finger from the lever operation portion 91 after accommodating the expansion portion 60 in the sheath 110, the medical device 10 enters the fourth state illustrated in FIGS. 4A and 4B described above. In the fourth state, the expansion portion 60 is held in contact with the inner peripheral surface of the sheath 110. Thereafter, the operator removes the medical device 10 from the blood vessel and completes the treatment using the medical device 10. The broken thrombus B is sucked and removed by, for example, the sheath 110 or other device.

As described above, the medical device 10 according to the present embodiment is for breaking up the thrombus B (object) in a living body lumen, the medical device 10 including: the long shaft portion 20 to be rotationally driven; the expansion portion 60 provided at the distal part of the shaft portion 20; the fixing portion 40 to which the distal end of the expansion portion 60 and the shaft portion 20 are fixed; the connection portion 70 fixed to the proximal end of the expansion portion 60 and movable in the axial direction with respect to the shaft portion 20; the outer tube 30 that accommodates the shaft portion 20 and is movable in the axial direction along the shaft portion 20; and the operation unit 80 to which the proximal part of the shaft portion 20 is rotatably connected, wherein the outer tube 30 includes the distal contact portion 32 disposed at the distal part and protruding radially outward, and the proximal contact portion 33 disposed at the proximal part, the operation unit 80 includes the housing 81 including the accommodating portion 85 in which the proximal part of the shaft portion 20 is disposed in a rotatable manner, the lever member 90 that is fixed to the outer tube 30, is movable in the axial direction with respect to the housing 81, and is partially accommodated in the accommodating portion 85, and an acting member (elastic member 84) capable of applying a force that moves the outer tube 30 in the distal direction to the outer tube 30 by movement of the outer tube 30 in the proximal direction, and when the acting member pushes the proximal contact portion 33 or the lever member 90 in the distal direction, the distal contact portion 32 is located proximal to the first restricting portion 72.

In the medical device 10 configured as described above, the distal contact portion 32 is located proximal to the first restricting portion 72, so that the distal contact portion 32 cannot press the first restricting portion 72 in the distal direction. Therefore, a force for expanding the expansion portion 60 does not act on the expansion portion 60 from the acting member. Accordingly, application of excessive force on the expansion portion 60 can be suppressed, whereby damage of a body tissue such as a blood vessel wall, the expansion portion 60, and the distal end of the sheath 110 can be prevented.

The force action length L1 over which the proximal contact portion 33 in the second state where the distal contact portion 32 presses the second restricting portion 73 toward the proximal side to contract the expansion portion 60 most in the radial direction is movable toward the distal side by receiving a force from the acting member (elastic member 84) inside the accommodating portion 85 is shorter than the distal-side displaceable length L2 over which the distal contact portion 32 is movable in the axial direction between the first restricting portion 72 and the second restricting portion 73. With this configuration, the distal contact portion 32 of the outer tube 30 currently receiving a force from the acting member cannot reach the first restricting portion 72 of the connection portion 70. Therefore, a force for expanding the expansion portion 60 does not act on the expansion portion 60 from the acting member. Accordingly, application of excessive force on the expansion portion 60 can be suppressed, whereby damage of a body tissue such as a blood vessel wall, the expansion portion 60, and the distal end of the sheath 110 can be prevented.

The proximal contact portion 33 is disposed on the proximal part of the outer tube 30 and protrudes radially outward. With this configuration, the proximal contact portion 33 is likely to receive a force from the acting member (elastic member 84) inside the accommodating portion 85.

The acting member is the elastic member 84 disposed in the accommodating portion 85. With this configuration, the distal contact portion 32 of the outer tube 30 currently receiving a repulsive force from the elastic member 84 cannot reach the first restricting portion 72 of the connection portion 70 in the medical device 10. Therefore, a force for expanding the expansion portion 60 does not act on the expansion portion 60 from the elastic member 84. Accordingly, application of excessive force on the expansion portion 60 can be suppressed, whereby damage of a body tissue such as a blood vessel wall, the expansion portion 60, and the distal end of the sheath 110 can be prevented.

In addition, the outer tube 30 is contactable to the elastic member 84 (acting member) without being fixed thereto. This configuration can prevent the outer tube 30 from receiving a force from the elastic member 84. Accordingly, application of excessive force on the expansion portion 60 from the elastic member 84 via the outer tube 30 can be suppressed, whereby damage of a body tissue such as a blood vessel wall, the expansion portion 60, and the distal end of the sheath 110 can be prevented.

The present invention is not limited to the above-described embodiment, and various modifications can be made by those skilled in the art within the technical idea of the disclosure here. For example, the living body lumen into which the medical device 10 is inserted is not limited to a blood vessel, and may be, for example, a vascular channel, a ureter, a bile duct, a fallopian tube, a hepatic duct, or the like. Therefore, the object to be broken up may not be the thrombus B.

Further, the wire rod 61 constituting the expansion portion 60 may not have a helical shape, and may be, for example, linear in the axial direction in a development diagram in the circumferential direction.

In addition, the acting member may not be the elastic member 84. For example, the acting member may be a member that connects the lever member 90 and the outer tube 30. The acting member may be integrally formed with the lever member 90.

REFERENCE SIGNS LIST

10 Medical device
20 Shaft portion
21 Shaft body
30 Outer tube
31 Outer tube body
32 Distal contact portion
33 Proximal contact portion
40 Fixing portion
50 Slide portion
60 Expansion portion
61 Wire rod
70 Connection portion
71 Distal-side fixing portion
72 First restricting portion
73 Second restricting portion
74 Cylindrical portion
80 Operation unit
81 Housing
84 Elastic member (acting member)
85 Accommodating portion
90 Lever member
91 Lever operation portion
92 Inner sliding portion
93 Outer tube fixing portion
94 Accommodation hole
100 Drive unit
B Thrombus (object)
L1 Force action length
L2 Distal-side displaceable length
L3 Movement allowable length

What is claimed is:

1. A medical device for breaking up an object in a living body lumen, the medical device comprising:

an elongated shaft portion to be rotationally driven;

an expansion portion provided at a distal part of the shaft portion;

a fixing portion to which a distal end of the expansion portion and the shaft portion are fixed;

a connection portion fixed to a proximal end of the expansion portion and movable in an axial direction with respect to the shaft portion;

an outer tube that accommodates the shaft portion and is movable in the axial direction along the shaft portion;

an operation unit to which a proximal part of the shaft portion is rotatably connected;

the outer tube including a distal contact portion disposed at a distal part of the outer tube and protruding radially outward, and a proximal contact portion disposed at a proximal part of the outer tube;

the connection portion including a first restricting portion that is disposed distal to the distal contact portion and fixes the slide portion, and a second restricting portion that is disposed proximal to the distal contact portion and through which the distal contact portion is unable to pass; and the operation unit including:

a housing including an accommodating portion in which the proximal part of the shaft portion is disposed in a rotatable manner;

a lever member that is fixed to the outer tube, is movable in the axial direction with respect to the housing, and is partially accommodated in the accommodating portion; and an acting member configured to apply a force that moves the outer tube in a distal direction to the outer tube by movement of the outer tube in a proximal direction;

when the acting member pushes the proximal contact portion or the lever member in the distal direction, the distal contact portion is located proximal to the first restricting portion; and wherein a force action length over which the proximal contact portion in a state where the distal contact portion presses the second restricting portion toward a proximal side of the device to contract the expansion portion most in the radial direction is movable toward a distal side of the device by receiving a force from the acting member inside the accommodating portion is shorter than a distal-side displaceable length over which the distal contact portion is movable in the axial direction between the first restricting portion and the second restricting portion.

2. The medical device according to claim 1, wherein the proximal contact portion is disposed on the proximal part of the outer tube and protrudes radially outward.

3. The medical device according to claim 1, wherein the acting member is an elastic member disposed in the accommodating portion.

4. The medical device according to claim 1, wherein the outer tube is contactable to the acting member without being fixed to the acting member.

5. A medical device positionable in a living body lumen to break-up an object in the living body lumen, the medical device comprising:

a rotatable elongated shaft connectable to a motor so that operation of the motor results in rotation of the shaft, the elongated shaft possessing a distal part;

a plurality of circumferentially spaced apart wires each possessing a proximal end and a distal end, the distal end of each of the plurality of wires being fixed relative to the distal part of the elongated shaft so that rotation of the elongated shaft results in rotation of the plurality of wires, the plurality of wires being movable into contact with the object in the living body lumen to break-up the object during rotation of the elongated shaft;

a connector axially movable along the elongated shaft and having a distal portion connected to the proximal ends of the wires so that axial movement of the connector results in axial movement of the proximal ends of the wires relative to the distal ends of the wires to radially expand the wires as the proximal ends of the wires move toward the distal ends of the wires and radially contract the wires as the proximal ends of the wires move away from the distal ends of the wires;

a tube that is axially movable relative to the elongated shaft, the tube including a projecting contact portion that is fixed relative to the tube so that axial movement of the tube results in axial movement of the projecting contact portion, the tube being axially movable relative to the connector in a proximal direction away from the wires until the projecting contact portion contacts a first part of the connector, and further axial movement of the tube relative to the connector in the proximal direction after the projecting contact portion contacts the first part of the connector resulting in axial movement of the connector in the proximal direction and radial contraction of the wires, the tube being axially movable relative to the connector in a distal direction toward the wires until the projecting contact portion contacts a second part of the connector located distal of the first part of the connector, and further axial movement of the tube relative to the connector in the proximal direction after the projecting contact portion contacts the first part of the connector resulting in axial movement of the connector in the proximal direction and radial contraction of the wires; and a compressible elastic member positioned to apply an elastic force to the tube when an external force external to the elastic member is applied to the elastic member so that the elastic member is in a compressed state, the elastic member being changeable from the compressed state to a natural state in which the external force is not applied to the elastic member, the tube being axially movable in the distal direction relative to the elongated shaft when the elastic member is in the natural state.

6. The medical device according to claim 5, wherein the elastic member is a spring.

7. The medical device according to claim 6, wherein the spring is positioned in a hollow accommodating portion in a housing, and the elongated shaft extends throughout an entire axial extent of the hollow accommodating portion of the housing.

8. The medical device according to claim 5, wherein the tube is connected to a movable lever so that movement of the lever results in axial movement of the tube.

9. The medical device according to claim 8, wherein the elastic member is positioned in a hollow accommodating portion in a housing, the lever including a portion that passes through a wall of the housing so that a part of the lever is outside the housing and a part of the lever connected to the tube is in the hollow accommodating portion in the housing.

10. The medical device according to claim 8, wherein the lever includes a tube fixing portion that is fixed to the tube, the tube fixing portion being located inside a housing, the elastic member also being located in the housing.

11. The medical device according to claim 5, wherein the elongated shaft passes through a housing in which is located a rotatable gear, the gear being fixed to the elongated shaft so that rotation of the gear results in rotation of the shaft and the plurality of wires, the gear being engageable with a part of the motor so that operation of the motor results in rotation of the gear.

12. The medical device according to claim 5, wherein the proximal ends of the wires are connected to the distal portion of the connector by virtue of the proximal ends of the wires being fixed to a slide portion that is held in a distal side fixing portion of the connector.

13. The medical device according to claim 5, wherein the tube is connected to an axially movable lever so that axial movement of the lever results in axial movement of the tube, the lever including an accommodation hole facing in the proximal direction, a distal portion of the tube being located in the accommodation hole, and a portion of the elastic member being located in the accommodation hole.

14. A medical device positionable in a living body lumen to break-up an object in the living body lumen in combination with a tubular sheath, the medical device comprising:

a rotatable elongated shaft connectable to a motor so that operation of the motor results in rotation of the shaft, the elongated shaft possessing a distal part;

a plurality of circumferentially spaced apart wires, each of the wires possessing a proximal end and a distal end, the distal end of each of the plurality of wires being fixed relative to the distal part of the elongated shaft so that rotation of the elongated shaft results in rotation of the plurality of wires, the plurality of wires being movable into contact with the object in the living body lumen to break-up the object during operation of the motor;

a connector axially movable along the elongated shaft and having a distal portion connected to the proximal ends of the wires so that axial movement of the connector results in axial movement of the proximal ends of the wires relative to the distal ends of the wires to radially expand the wires as the proximal ends of the wires move toward the distal ends of the wires and radially contract the wires as the proximal ends of the wires move away from the distal ends of the wires;

a tube that is axially movable relative to the elongated shaft, the tube including a projecting contact portion that is fixed relative to the tube so that axial movement of the tube results in axial movement of the projecting contact portion, the tube being axially movable relative to the connector in a proximal direction away from the wires until the projecting contact portion contacts a first part of the connector, and further axial movement of the tube relative to the connector in the proximal direction after the projecting contact portion contacts the first part of the connector resulting in axial movement of the connector in the proximal direction and radial contraction of the wires, the tube being axially movable relative to the connector in a distal axial direction toward the wires until the projecting contact portion contacts a second part of the connector located distal of the first part of the connector;

a compressible elastic member that is in a natural state when no external force external to the elastic member is applied to the elastic member, the elastic member being changeable from the natural state to a compressed state when the external force external to the elastic member is applied to the elastic member to compress the elastic member, the elastic member being positioned to apply an elastic force to the tube when the elastic member is in the compressed state;

the plurality of wires: i) being positionable inside the tubular sheath while the wires are radially contracted as a result of the axial movement of the tube relative to the connector in the proximal direction after the projecting contact portion contacts the first part of the connector so that the wires contact an inner periphery of the tubular sheath; and ii) when positioned inside the tubular sheath are releasable from the tubular sheath so that the wires expand by their own elastic force and return to a natural state allowing the wires to be brought into contact with the object in the living body lumen; and when the wires are positioned in the tubular sheath, a force in the distal axial direction from the elastic member does not act on the tube.

15. The medical device in combination with the tubular sheath according to claim 14, wherein the elastic member is positioned in a hollow accommodating portion located inside a housing.

16. The medical device in combination with the tubular sheath according to claim 15, wherein the tube is connected to a movable lever so that movement of the lever results in the axial movement of the tube, a part of the lever being located outside the housing and movable relative to the housing, another part of the lever passing through an opening in the housing and being fixed to the tube.

17. The medical device in combination with the tubular sheath according to claim 15, wherein the elastic member is a spring.

18. The medical device in combination with the tubular sheath according to claim 17, wherein the elongated shaft passes through the housing in which is located the spring, a proximal portion of the tube being located in the housing.

19. The medical device in combination with the tubular sheath according to claim 15, wherein the proximal ends of the wires are connected to the distal portion of the connector by virtue of the proximal ends of the wires being fixed to a slide portion that is held in a distal side fixing portion of the connector.

20. A medical device for breaking up an object in a living body lumen, the medical device comprising:

an elongated shaft portion to be rotationally driven;

an expansion portion provided at a distal part of the shaft portion;

a fixing portion to which a distal end of the expansion portion and the shaft portion are fixed;

a connection portion fixed to a proximal end of the expansion portion and movable in an axial direction with respect to the shaft portion;

an outer tube that accommodates the shaft portion and is movable in the axial direction along the shaft portion;

an operation unit to which a proximal part of the shaft portion is rotatably connected;

the outer tube including a distal contact portion disposed at a distal part of the outer tube and protruding radially outward, and a proximal contact portion disposed at a proximal part of the outer tube;

the connection portion including a first restricting portion that is disposed distal to the distal contact portion and fixes a slide portion, and a second restricting portion that is disposed proximal to the distal contact portion and through which the distal contact portion is unable to pass; and the operation unit including:

a housing including an accommodating portion in which the proximal part of the shaft portion is disposed in a rotatable manner;

a lever member that is fixed to the outer tube, is movable in the axial direction with respect to the housing, and is partially accommodated in the accommodating portion; and an acting member configured to apply a force that moves the outer tube in a distal direction to the outer tube by movement of the outer tube in a proximal direction;

when the acting member pushes the proximal contact portion or the lever member in the distal direction, the distal contact portion is located proximal to the first restricting portion; and wherein the outer tube is contactable to the acting member without being fixed to the acting member.

* * * * *